(12) United States Patent
Cooke et al.

(10) Patent No.: US 8,137,288 B2
(45) Date of Patent: *Mar. 20, 2012

(54) MEDICAL INSTRUMENT

(75) Inventors: David Cooke, Harvard, MA (US); Hanspeter Robert Bayer, Meriden, CT (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 292 days.

This patent is subject to a terminal disclaimer.

(21) Appl. No.: 12/166,099

(22) Filed: Jul. 1, 2008

(65) Prior Publication Data

US 2008/0269638 A1    Oct. 30, 2008

Related U.S. Application Data

(63) Continuation-in-part of application No. 10/855,248, filed on May 27, 2004, now abandoned, which is a continuation-in-part of application No. 11/325,837, filed on Jan. 4, 2006, now Pat. No. 7,449,000, which is a continuation of application No. 10/300,512, filed on Nov. 20, 2002, now Pat. No. 7,008,382.

(51) Int. Cl.
    *A61B 10/00* (2006.01)
(52) U.S. Cl. .................................................. 600/564
(58) Field of Classification Search .......... 600/562–568; 606/167, 170
    See application file for complete search history.

(56) References Cited

U.S. PATENT DOCUMENTS

| | | |
|---|---|---|
| 4,274,414 A | 6/1981 | Johnson et al. |
| 4,844,064 A | 7/1989 | Thimsen et al. |
| 4,924,878 A | 5/1990 | Nottke |
| 4,953,558 A | 9/1990 | Akerfeldt |
| 5,195,533 A | 3/1993 | Chin et al. |
| 5,368,045 A | 11/1994 | Clement et al. |
| 5,476,101 A | 12/1995 | Schramm et al. |
| 5,507,298 A | 4/1996 | Schramm et al. |
| 5,660,186 A | 8/1997 | Bachir |
| 5,685,852 A | 11/1997 | Turkel et al. |
| 5,718,237 A | 2/1998 | Haaga |
| 5,779,647 A | 7/1998 | Chau et al. |
| 5,842,999 A | 12/1998 | Pruitt et al. |
| 5,989,196 A | 11/1999 | Chu et al. |
| 5,993,399 A | 11/1999 | Pruitt et al. |
| 6,015,391 A | 1/2000 | Rishton et al. |
| 6,033,411 A | 3/2000 | Preissman |
| 6,050,955 A | 4/2000 | Bryan et al. |
| 6,086,543 A | 7/2000 | Anderson et al. |
| 6,126,617 A | 10/2000 | Weilandt et al. |
| 6,142,955 A | 11/2000 | Farascioni et al. |
| 6,165,136 A | 12/2000 | Nishtala |
| 6,221,030 B1 | 4/2001 | Avaltroni |

(Continued)

FOREIGN PATENT DOCUMENTS

DE    100 34 297    4/2001

(Continued)

*Primary Examiner* — Brian Szmal
(74) *Attorney, Agent, or Firm* — Fish & Richardson P.C.

(57) ABSTRACT

Medical instruments and methods of using the instruments are described. In some embodiments, a medical instrument includes a housing, a stylet having a portion in the housing, a movable first member in the housing, the movable member being connected to the stylet, and a second member located in the housing to reduce movement of the first member. The second member is configured to change movement of the first member from a first direction to a second direction different than the first direction.

18 Claims, 9 Drawing Sheets

U.S. PATENT DOCUMENTS

| | | |
|---|---|---|
| 6,293,957 B1 | 9/2001 | Peters et al. |
| 6,358,217 B1 | 3/2002 | Bourassa |
| 6,402,701 B1 | 6/2002 | Kaplan et al. |
| 6,428,486 B2 | 8/2002 | Ritchart et al. |
| 6,488,636 B2 | 12/2002 | Bryan et al. |
| 6,497,706 B1 | 12/2002 | Burbank et al. |
| 6,544,192 B2 | 4/2003 | Starr et al. |
| 6,620,111 B2 | 9/2003 | Stephens et al. |
| 6,730,045 B2 | 5/2004 | Finer |
| 6,849,080 B2 | 2/2005 | Lee et al. |
| 7,008,382 B2 | 3/2006 | Adams et al. |
| 7,022,085 B2 | 4/2006 | Cooke et al. |
| 7,201,722 B2 | 4/2007 | Krueger |
| 7,449,000 B2 * | 11/2008 | Adams et al. .................. 600/564 |
| 2008/0269638 A1 | 10/2008 | Cooke et al. |

FOREIGN PATENT DOCUMENTS

| | | |
|---|---|---|
| EP | 0 536 888 | 4/1993 |
| JP | 1-198537 | 8/1989 |
| JP | 4-506758 | 11/1992 |
| JP | 6-197898 | 7/1994 |
| JP | 10-179592 | 7/1998 |
| JP | 2000-506044 | 5/2000 |
| JP | 2002-000609 | 1/2002 |
| JP | 2002-514458 | 5/2002 |

* cited by examiner

MEDICAL INSTRUMENT

RELATED APPLICATIONS

This application is a continuation-in-part of U.S. application Ser. No. 10/855,248, filed May 27, 2004; and is a continuation-in-part to U.S. application Ser. No. 11/325,837, filed Jan. 4, 2006, which is a continuation of U.S. application Ser. No. 10/300,512, filed Nov. 20, 2002, now U.S. Pat. No. 7,008,382. All three prior applications are incorporated herein by reference in their entirety.

TECHNICAL FIELD

The invention relates to medical instruments, such as a biopsy needle instrument.

BACKGROUND

A biopsy needle instrument can be used to obtain a tissue specimen for microscopic examination, e.g., to determine malignancy, while preferably subjecting the patient to the least trauma. In some embodiments, such instruments can have of a long, thin probe, called a stylet, within a close-fitting hollow needle, called a cannula. The stylet has a notch into which tissue can prolapse when the stylet enters the tissue.

During use, a firing device first projects the stylet into tissue, followed immediately by the cannula. As the cannula slides over the stylet, the cannula severs tissue that has prolapsed into the notch of the stylet from the surrounding mass, and captures the prolapsed tissue as a specimen within the notch. The instrument can then be withdrawn and the piece of tissue removed from the stylet.

SUMMARY

The invention relates to medical instruments, such as a biopsy needle instrument.

In some circumstances, when a biopsy needle instrument is fired to propel a stylet, the stylet can rebound or kick back at the end of its travel. This kick back can reduce the accuracy of the instrument. In one aspect, the invention features a medical instrument having reduced kick back of the stylet.

In another aspect, the invention features a medical instrument, including a housing, a stylet having a portion in the housing, a movable first member in the housing, the movable member being connected to the stylet, and a second member located in the housing to reduce movement of the first member, the second member configured to change movement of the first member from a first direction to a second direction different than the first direction.

Embodiments may include one or more of the following features. The second member includes a raised portion configured to contact the movable first member. The raised portion is off-centered relative to a longitudinal axis of the instrument. The housing includes a recessed portion capable of accommodating a portion of the movable first member. The relief portion is on a side wall of the housing. The instrument further includes a cannula having a portion in the housing, and a movable third member connected to the cannula, wherein the second member is between the first member and the third member. The instrument further includes a pivotable latch capable of holding and releasing the movable third member. The instrument further includes a pivotable latch capable of holding and releasing the movable first member. The instrument further includes a first trigger capable of engaging the pivotable latch to release the movable first member. The instrument further includes a second trigger capable of engaging the pivotable latch to release the movable first member. The first trigger is located at a distal end of the housing. The first trigger is located between a distal end and a proximal end of the housing.

In another aspect, the invention features a medical instrument, including a housing, a movable stylet block in the housing, a stylet connected to the stylet block, a movable cannula block in the housing, a cannula connected to the cannula block, and a stop between the stylet block and the cannula block, the stop configured to contact the stylet block off-centered relative to a center longitudinal axis of the medical instrument.

Embodiments may include one or more of the following features. The stop includes a raised portion configured to contact the stylet block off-centered. The housing includes a recessed portion configured to accommodate a portion of the stylet block. The instrument further includes a pivotable latch capable of holding and releasing the cannula block. The instrument further includes a pivotable latch capable of holding and releasing the stylet block. The instrument further includes two triggers, either trigger capable of pivoting the latch to release the stylet block.

In another aspect, the invention features a method of operating a medical instrument. The method can include moving a first member connected to a stylet from a retracted position to an extended position, and changing the direction of movement of the first member from a first direction to a second direction.

Embodiments may include one or more of the following features. Changing the direction of movement of the first member includes rotating the first member. The method includes rotating the first member relative to an axial axis of the medical instrument. Changing the movement of the first member includes contacting the first member against a portion of the medical instrument off-centered relative to a longitudinal axis of the medical instrument. The method further includes stopping the movement of the first member. Movement of the first member is stopped and changed substantially simultaneously. The method further includes moving a portion of the first member towards a recessed portion of the medical instrument. The method further includes pivoting a latch holding a cannula in a retracted position to release the cannula. The method further includes activating a trigger at a distal end of the medical instrument to move the first member. Activating the trigger pivotally releases a latch holding the first member in the retracted position. The method further includes activating a trigger between the distal end and the proximal end of the medical instrument to move the first member. Activating the trigger pivotally releases a latch holding the first member in the retracted position.

In another aspect, the invention features a method of operating a medical instrument, including moving a first member connected to a stylet, and contacting the first member against a second member located off-centered relative to a longitudinal axis of the instrument. The method can further include moving a portion of the first member into a recessed portion of the instrument. The method can further include rotating the first member.

Other aspects, features, and advantages of the invention will be apparent from the description of the preferred embodiments thereof and from the claims.

DETAILED DESCRIPTION

Figure 1:
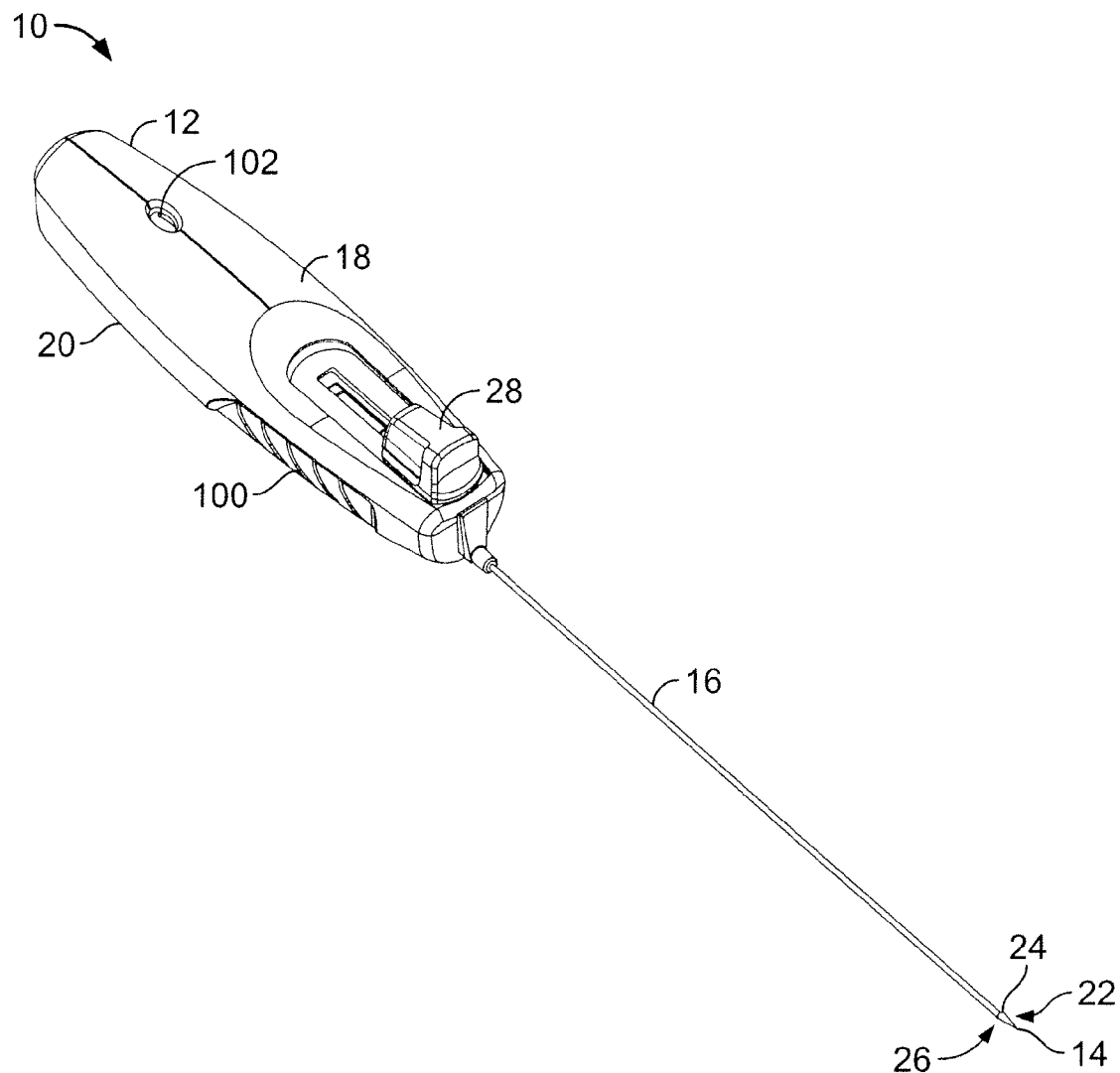
FIG. 1 is a perspective view of a biopsy needle instrument.

Referring to FIG. 1, a needle biopsy device 10 includes a housing 12, a stylet 14, and a cannula 16 coaxially receiving the stylet. Housing 12 includes a top shell 18 and a bottom shell 20 configured to mate together to form the housing. At its distal end 22, stylet 14 is configured to penetrate tissue and includes a cupped notch 24 configured to collect a tissue sample. At its distal end 26, cannula 16 is configured to sever tissue that has prolapsed into notch 24. Both stylet 14 and cannula 16 extend proximally toward housing 12 and have portions inside the housing 12. Stylet 14 and cannula 16 can be moved between retracted positions and extended positions. During use, stylet 14 and cannula 16 are loaded or cocked to their retracted positions, ready to be triggered, by moving a load button 28 proximally. When stylet 14 and cannula 16 are fired, they rapidly move distally to their extended positions, e.g., to collect a tissue specimen that has prolapsed into notch 24 of the stylet.

Figure 2A:
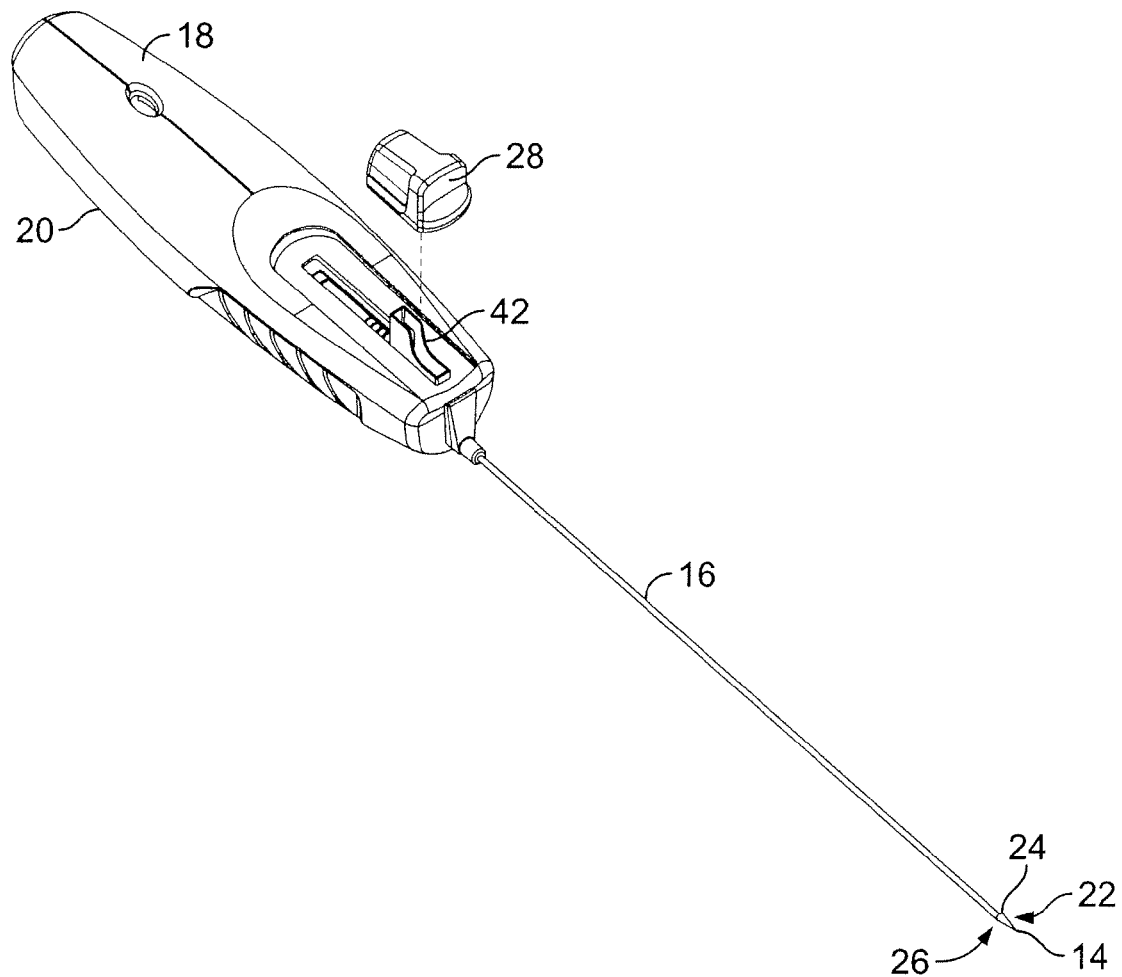
FIGS. 2A, 2B, 2C, 2D, and 2E are exploded, perspective views of the instrument of FIG. 1, at various stages of assembly.
Figure 2B:
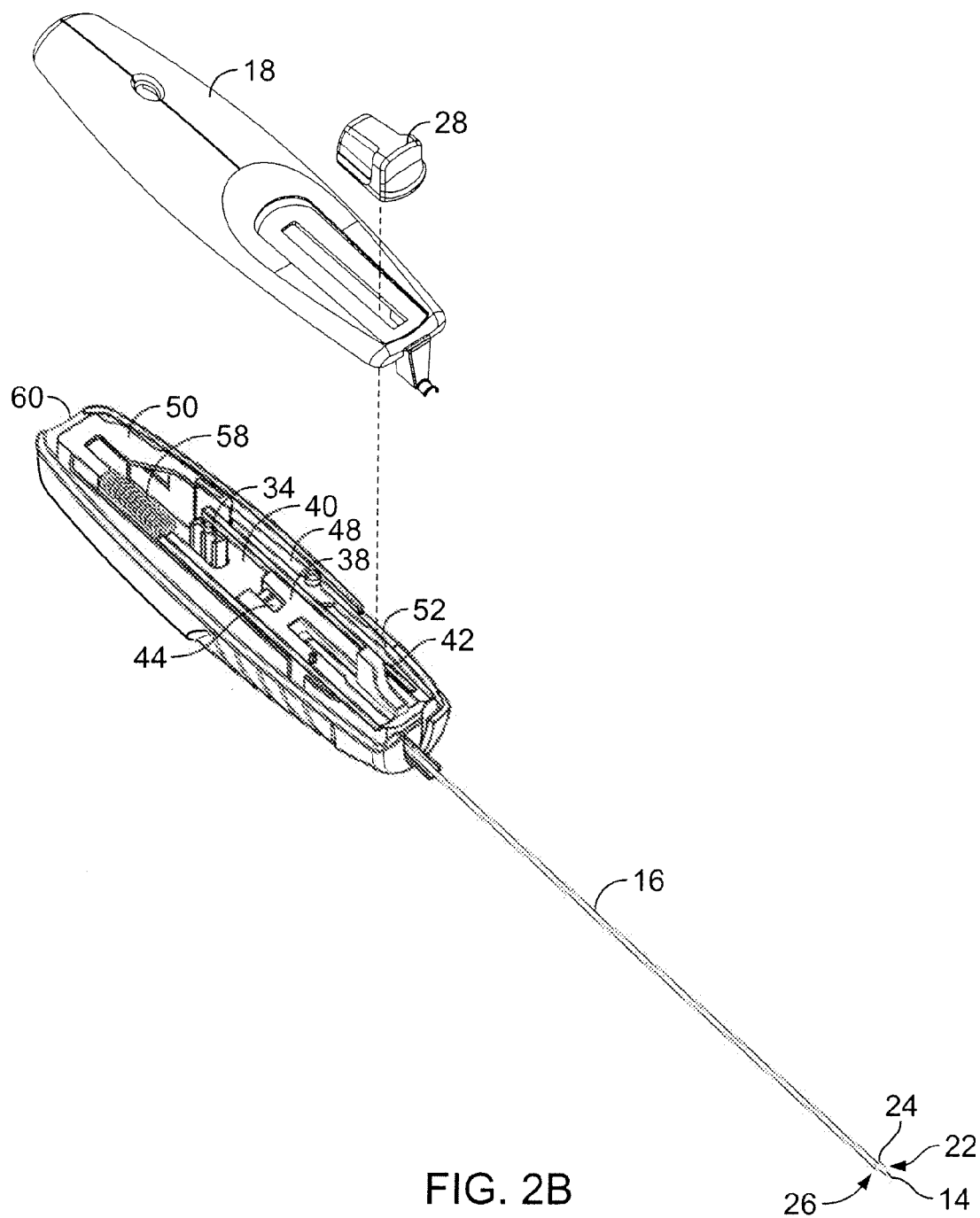
Figure 2C:
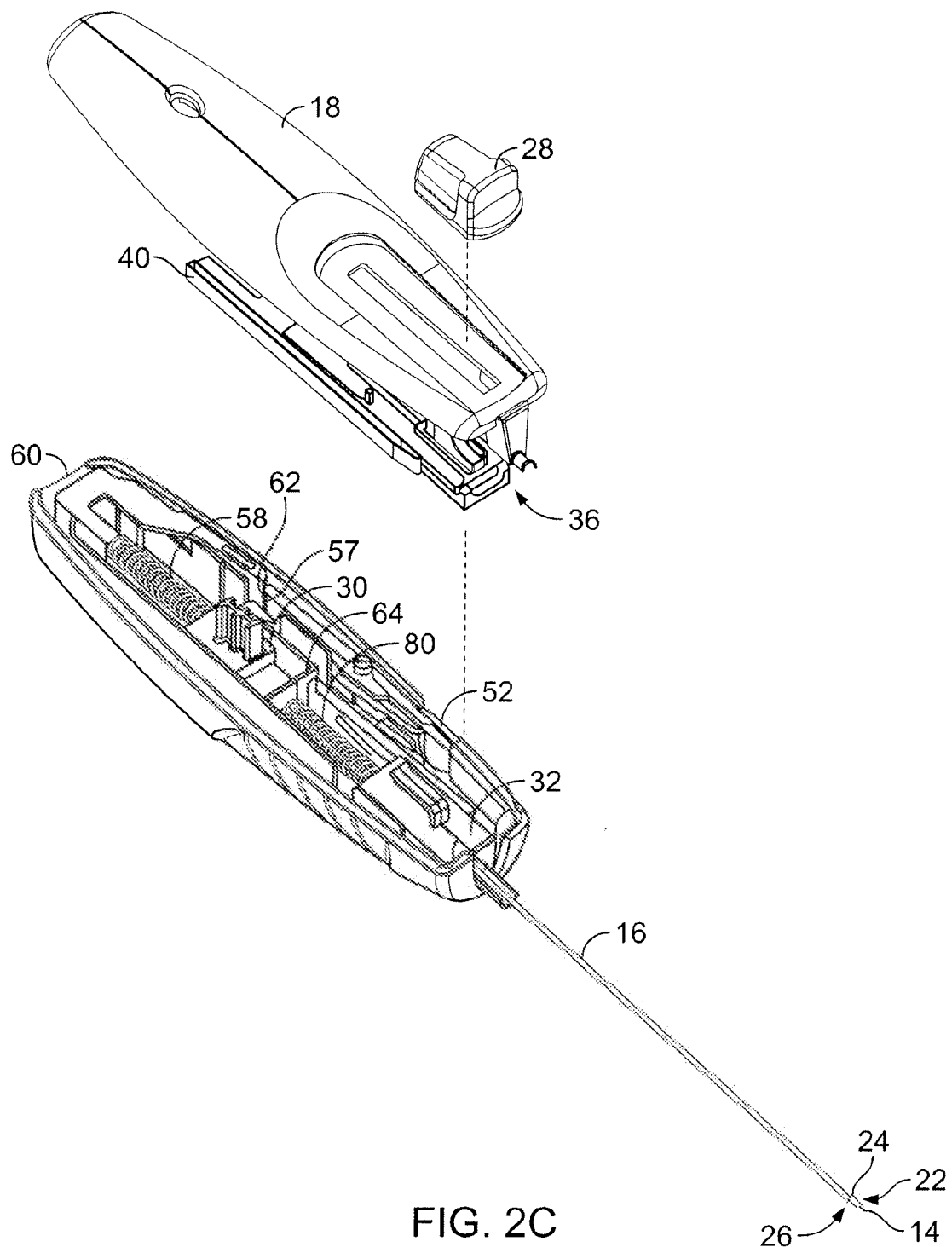
Figure 2D:
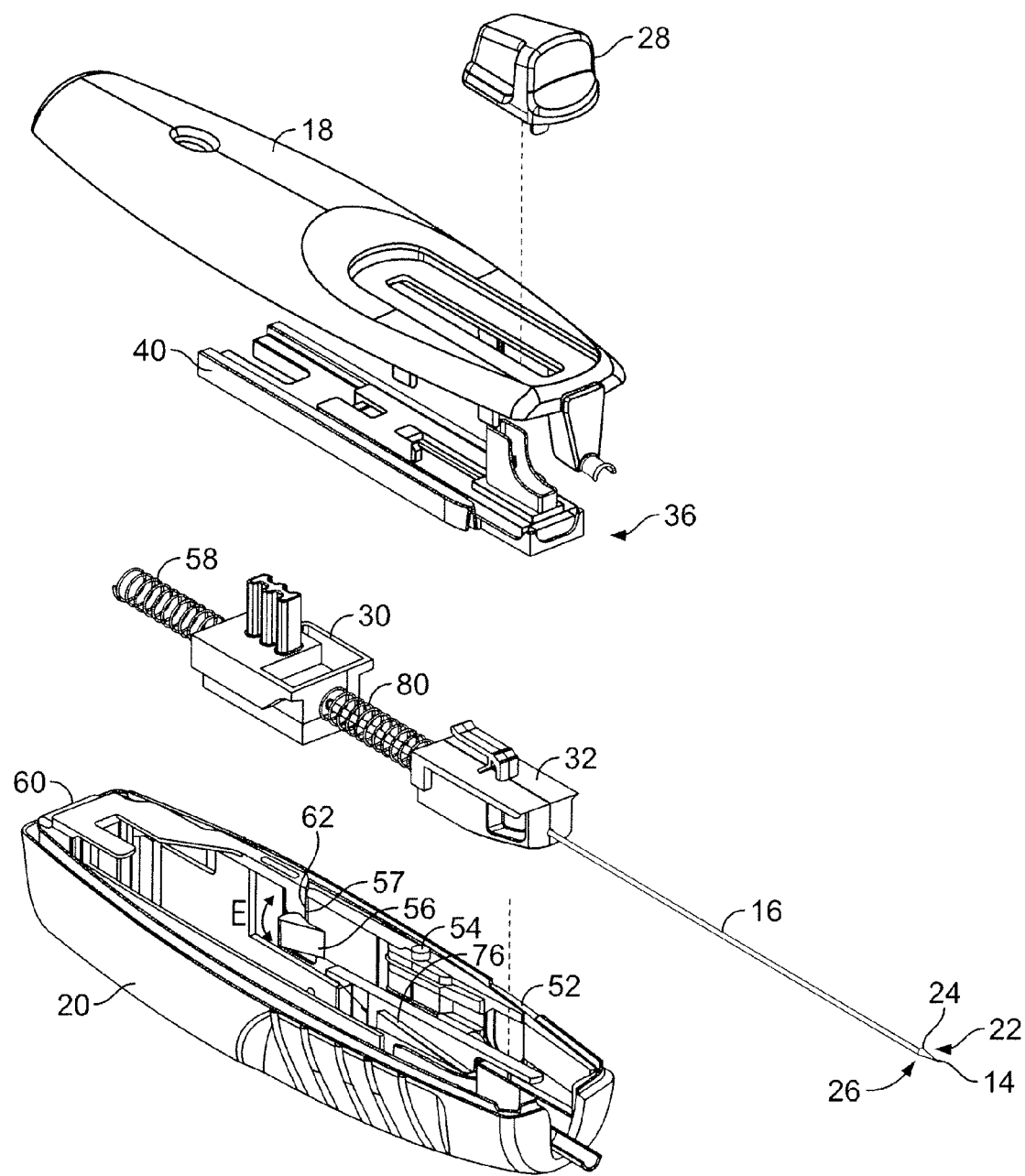
Figure 2E:
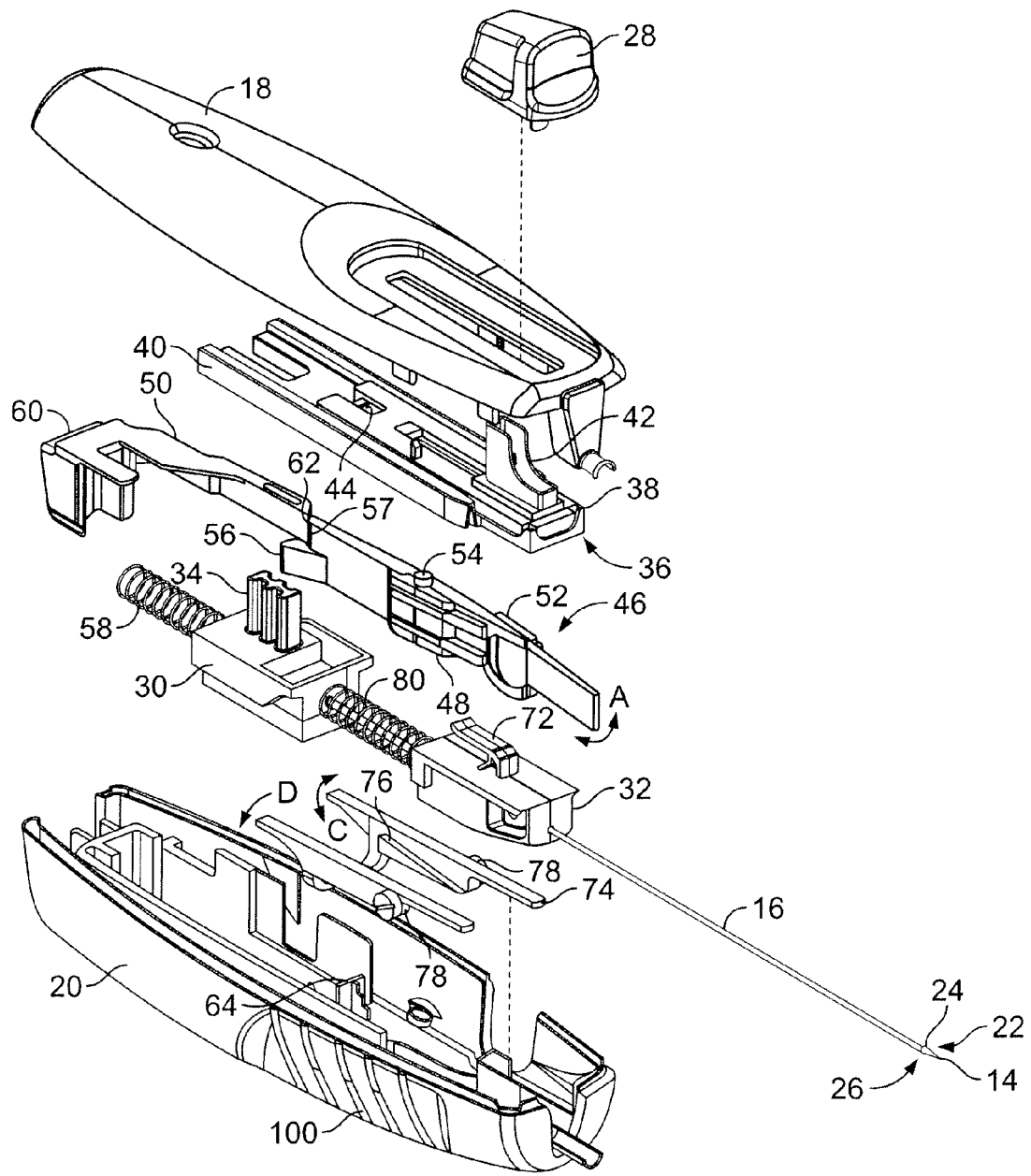

Referring to FIGS. 2A-2E, particularly to FIG. 2E, at their proximal ends, stylet 14 and cannula 16 are connected to a movable stylet block 30 and a movable cannula block 32, respectively. Stylet block 30 is configured to be movable to a retracted position, where the stylet block can be held, and subsequently, selectively released. Stylet block 30 includes a post 34 configured to engage with a loading mechanism 36. Loading mechanism 36 includes a slidable member 38 slidably received on a platform 40 that rests on stylet block 30 and cannula block 32 (FIG. 2B). Slidable member 38 includes a projection 42 configured to attach to (e.g., snap in with) load button 28, and a notch 44 configured to engage with post 34 of stylet block 30. Thus, as load button 28 is moved proximally, notch 44 engages with post 34 to move stylet block 30 (and connected stylet 14) proximally to their retracted positions where they can be held by a stylet latch 46.

Stylet latch 46 is configured to hold stylet block 30 in a retracted position, and to release the stylet block selectively. Stylet latch 46 includes a distal component 48 and a proximal component 50. Distal component 48 includes a side trigger 52, a pivot 54, and a wedge-shaped portion 56. At its proximal end, distal component 48 has an angled surface 57 that engages with the distal end of proximal component 50, as described below. Portion 56 is configured to allow stylet block 30 to slide to its retracted position, and thereafter, to engage with the stylet block (at the proximal face of the stylet block) to hold the stylet block in its retracted position. Side trigger 52 is located on the outside of housing 12 when device 10 is fully assembled. When side trigger 52 is pushed toward housing 12, distal component 48 pivots about pivot 54 (arrow A), which moves wedge-shaped portion 56 out of engagement with stylet block 30. When released from portion 56, stylet block 30 is capable of moving distally under the spring force of a stylet spring 58. Alternatively, stylet block 30 can be moved out of engagement with wedge-shaped portion 56 by operating proximal component 50 of stylet latch 46. As shown, the area of distal component 48 near pivot 54 is formed relatively thick to provide good stiffness, and the area of the distal component at side trigger 52 is formed relatively thin to allow the distal component to flex as well as to provide clearance with other components in device 10 as the side is pushed in. The angled portion between pivot 54 and side trigger 52 provides a quick transition from the thick area to the thin area. The angled distal end of distal component 48 helps to keep side trigger 52 positioned outside of housing 12.

Proximal component 50 includes a rear trigger 60, and an angled surface 62 at the distal end of the proximal component. When rear trigger 60 is pushed proximally, angled surface 62 engages with (e.g., rides on) angled surface 57 of distal component 48, thereby causing distal component 48 to pivot about pivot 54 (arrow A) and moving wedge-shaped portion 56 out of engagement with stylet block 30 (arrow E, FIG. 2D). Thus, stylet block 30 can be fired by pushing either side trigger 52 or rear trigger 60.

Figure 3:
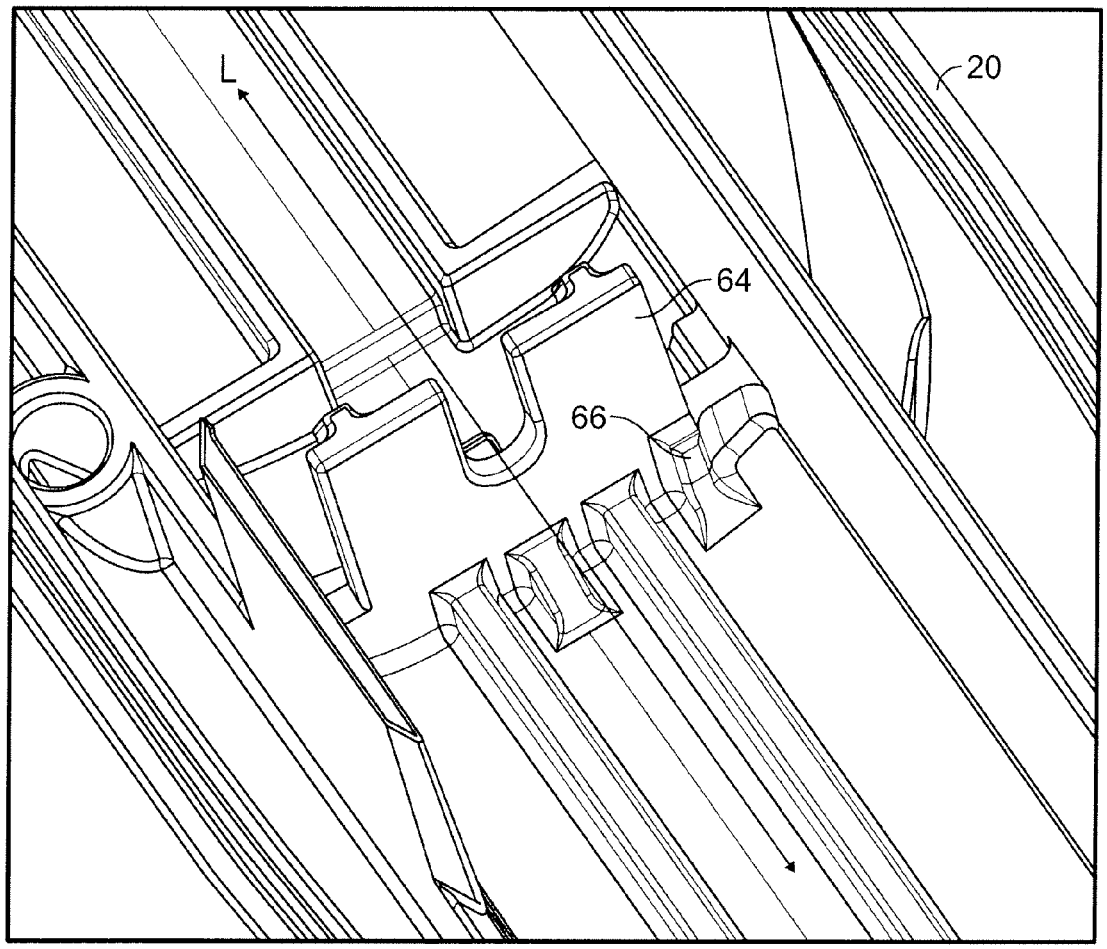
FIG. 3 is a perspective view of a portion of a housing of the instrument of FIG. 1.
Figure 4:
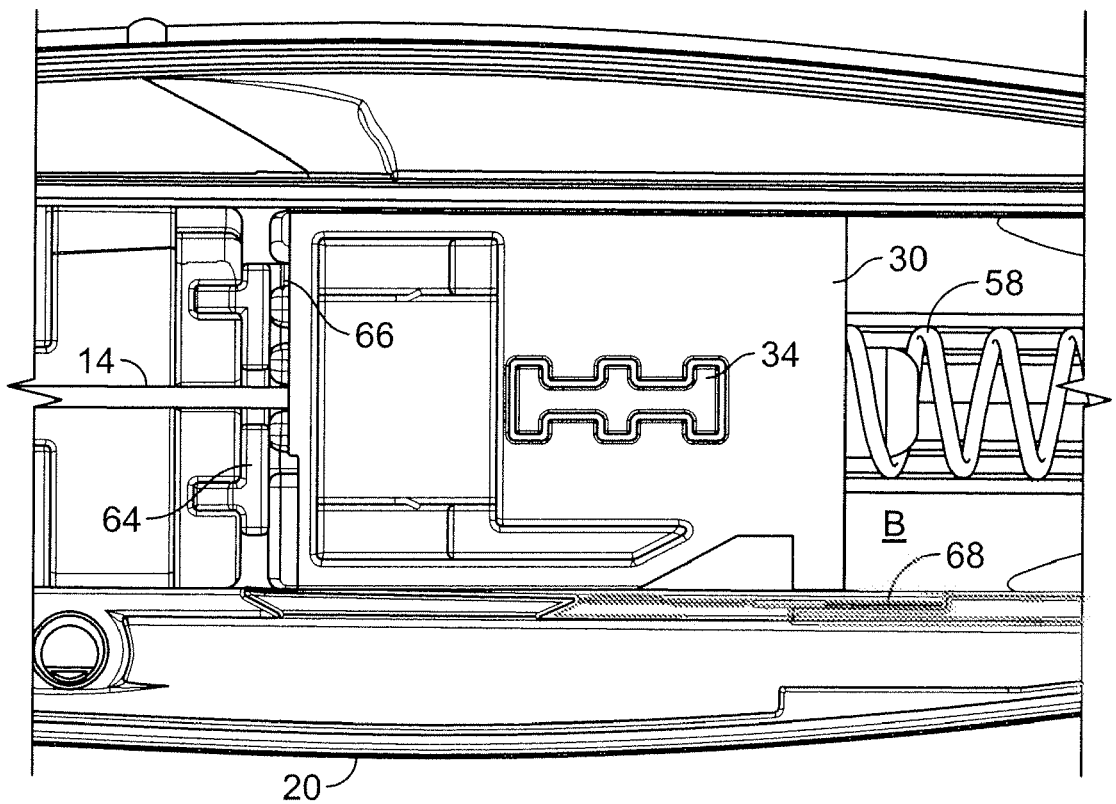
FIG. 4 is a perspective top view of a stylet block of the instrument of FIG. 1.
Figure 5:
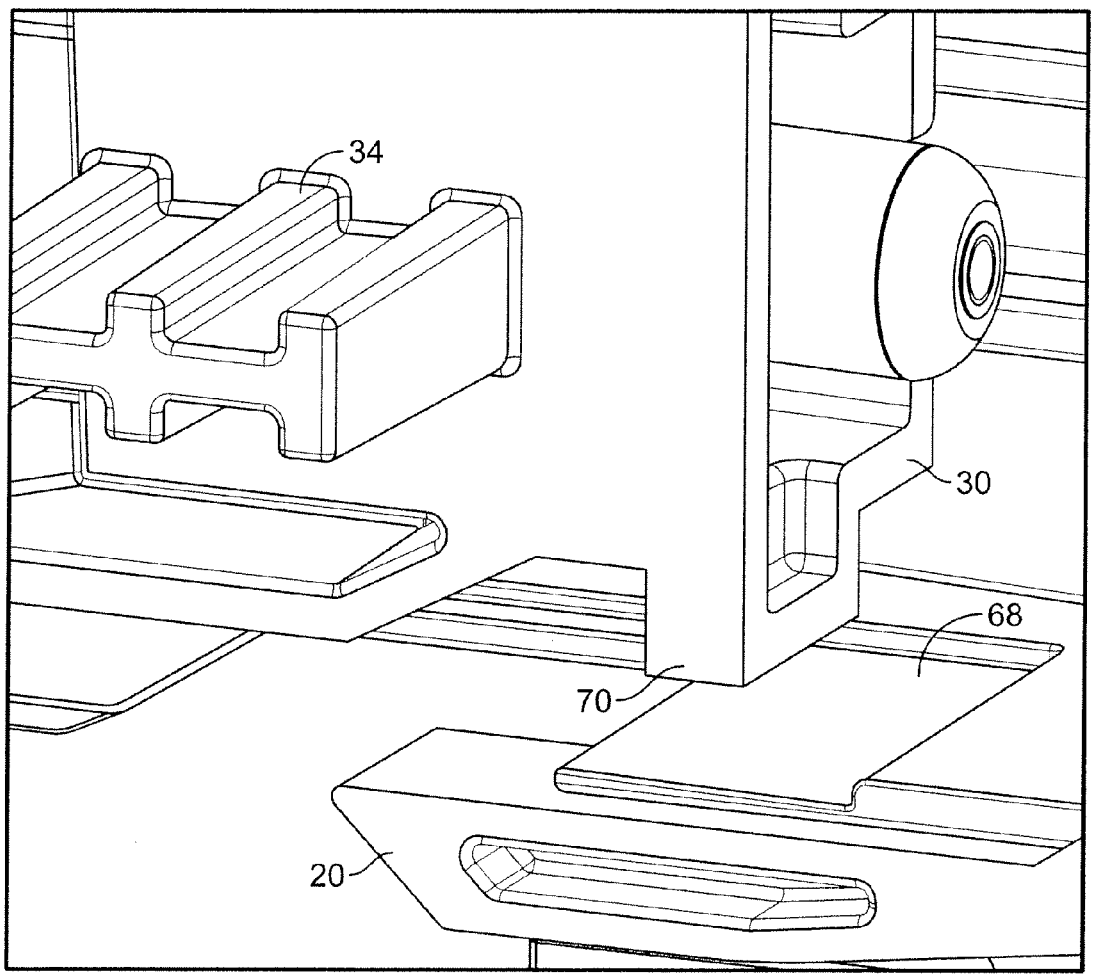
FIG. 5 is a perspective view of a portion of the stylet block and the housing of the instrument of FIG. 1.

After stylet block 30 is fired, device 10 is configured to stop and to deflect the movement of the stylet block. Referring further to FIGS. 3, 4, and 5, bottom shell 20 of housing 12 includes a stop member 64 located between stylet block 30 and cannula block 32. On the proximal side of stop member 64, bottom shell 20 includes a rib or a raised portion 66 located off-center relative to the center longitudinal axis (L) of device 10. As shown, rib 66 is formed at a lower corner of stop member 64 (e.g., by molding), but in other embodiments, the rib can be formed anywhere off-center of longitudinal axis L. Rib 66 is high enough for stylet block 30 to contact when the stylet block reaches its end point of travel. Referring particularly to FIG. 5, bottom shell 20 further includes a recessed portion or a relief 68 configured to accommodate a portion 70 of stylet block 30 (as shown, a rear corner).

During use, after side trigger 52 or rear trigger 60 is activated, stylet block 30 is propelled distally toward stop member 64. Stylet block 30 then strikes rib 66, which causes the stylet block to rotate or to deflect (arrow B, FIG. 4). In other words, when stylet block 30 strikes rib 66, the movement of the stylet block is changed from a first direction (e.g., generally linearly and distally) to a second direction (e.g., sideways). It is believed that the deflection can also slightly misalign cannula 16 and stylet 14 to create friction to dissipate energy that may otherwise create kickback. No kinetic energy is believed to be dissipated until the end of the travel of stylet block 30, such that the speed of stylet 14 during travel is enhanced (e.g., maximized) and the energy that is dissipated at the end of travel is excess energy. Rotation of stylet block 30 also moves portion 70 of the stylet block into recessed portion 68. As a result, stylet block 30 is prevented from hitting stop member 64 and rebounding or kicking back, which can cause inaccurate sampling of tissue.

Referring particularly to FIG. 2E, cannula block 32 is configured to be movable to a retracted position, where the cannula block can be held, and subsequently, selectively released. Cannula block 32 includes a cannula post 72 configured to engage with slidable member 38 of loading mechanism 36 (FIG. 2B). As load button 28 is moved proximally, slidable member 38 engages with cannula post 72 to move cannula block 32 (and connected cannula 16) proximally to their retracted positions, where they can be held by a cannula latch 74.

Cannula latch 74 is configured to hold cannula block 32 in a retracted position, and to selectively release the cannula block. Cannula latch 74 includes two identical wedge-shaped portions 76 (only one of which is visible in FIG. 2E) and a pivot 78. Wedge-shaped portions 76 are configured to allow cannula block 32 to slide to its retracted position, and thereafter, to engage with cannula block (at the proximal face of the cannula block) to hold the cannula block in its retracted position. Pivot 78 allows cannula latch 74 to seesaw (arrow C) so that cannula block 32 can be moved to and locked in its retracted position, and subsequently released. During use, when stylet block 30 is released from its retracted position and moves distally, the stylet block engages cannula latch 74 and pivots the cannula latch (arrow D). As a result, wedge-shaped portions 76 pivot out of engagement with and release cannula block 32. Cannula block 32 is then capable of moving distally under the spring force of a cannula spring 80.

Examples of suitable stylet 14 and cannula 16 configurations are exemplified by the ASAP™ Automated Biopsy System having a Delta Cut® needle or a Channel Cut® needle (available from Boston Scientific Corp., Natick, Mass.), and described in Chu, U.S. Pat. No. 5,989,196, and commonly assigned U.S. Ser. No. 10/728,248, filed Dec. 4, 2003, hereby incorporated by reference.

The components of device 10 (e.g., housing 12, latches 46 and 74, stylet block 30, or cannula block 32) described above can be formed by injection molding techniques, e.g., of polycarbonate and/or ABS. Stylet 14, cannula 16, and springs 58 and 80 can be formed of stainless steel.

In operation, cannula 16 and stylet 14 are loaded (e.g., moved proximally and retained in their retracted positions) and subsequently fired (e.g., released and propelled distally). More specifically, device 10 is loaded by moving load button 28 proximally, which moves cannula block 32 proximally via slidable member 38 and cannula post 72. Cannula block 32 is moved proximally past wedge-shaped portions 76, where the cannula block is held in its retracted position by portions 76. Cannula spring 80 is compressed between stop member 64 and cannula block 32. Moving load button 28 further proximally moves stylet block 30 proximally via notch 44 of slidable member 38 and post 34. Stylet block 30 is moved proximally past wedge-shaped portion 56, where the stylet block is held in its retracted position by portion 56. Stylet spring 58 is compressed between a portion of bottom shell 20 and stylet block 30. Device 10 is loaded and ready to be fired.

To fire device 10, distal end 22 of stylet 14 is placed adjacent to a target area, and either side trigger 52 or rear trigger 60 is actuated. For example, actuating side trigger 52 causes stylet latch 46 to pivot about pivot 54 (arrow E, FIG. 2D), thereby moving wedge-shaped portion 56 out of engagement with stylet block 30 and releasing the stylet block. Upon disengagement, stylet block 30 and stylet 14 are propelled distally by the spring force of stylet spring 58, which allows the stylet to penetrate the targeted area, e.g., tissue. Stylet block 30 then strikes rib 66 and rotates (arrow B, FIG. 4), which causes portion 70 of the stylet block to enter into recessed portion 68 of bottom shell 20. As discussed above, this deflection of stylet block 30 dissipates energy from stylet spring 58, reduces rebound of the stylet block and enhances accuracy of the device.

Substantially simultaneously with striking rib 66, stylet block 30 also engages and pivots cannula latch 74 about pivot 78 (arrow D, FIG. 2E). Pivoting cannula latch 74 disengages wedge-shaped portions 76 from cannula block 32. Upon disengagement or release, cannula block 32 and cannula 16 are propelled distally by the spring force of cannula spring 80, which allows the cannula to slide over stylet 14 and to sever a specimen that has prolapsed into notch 24 of the stylet.

Device 10 can then be withdrawn from the targeted area. The specimen can be removed from notch 24 by first retracting cannula 16 and cannula block 32 proximally. The specimen can be placed on a slide or in a preservative solution. If desired, stylet 14 can be retracted to load device 10 and to collect another specimen.

In other embodiments, the features described above, such as rib 66 and/or recessed portion 68, can be incorporated into other embodiments of needle biopsy devices. Other embodiments of needle biopsy devices are described in commonly assigned U.S. Ser. No. 10/300,249, filed Nov. 20, 2002; U.S. Ser. No. 10/300,512, filed Nov. 20, 2002; and U.S. Ser. No. 10/728,248, filed Dec. 4, 2003, hereby incorporated by reference.

In some embodiments, housing 12 can be made of different materials, e.g., to enhance the grip or "feel" of device 10. For example, housing 12 can be formed of materials with different hardness, e.g., a core of relatively hard material and an outer layer of relatively soft material. The outer layer can be a foamy material, such as a urethane, to enhance the grip and/or to absorb vibrations from the firing of device 10. Housing 12 can be formed with two or more different materials. For example, as shown in FIG. 1, device 10 includes side portions 100 formed of different materials to enhance grip and comfort.

In other embodiments, referring to FIG. 1, housing 12 includes an opening 102 that, together with stylet block 30, can provide a visual indication that device 10 is loaded. More specifically, when stylet block 30 is loaded to its retracted position, the stylet block can be seen through opening 102. In some embodiments, stylet block 30 is formed of a bright color, e.g., red, to enhance its visibility.

Terms such as "side", "top" and "bottom" are used to describe embodiments as shown in the orientation of the figures and not intended to be limiting.

Other embodiments are within the claims.

What is claimed is:

1. A medical instrument, comprising:
a housing;
a stylet having a portion in the housing;
a movable first member in the housing, the movable first member being connected to the stylet;
a stop in contact with and extending a first distance from a bottom wall of the housing in a first direction; and
a second member in contact with and extending axially from the stop, the second member in contact with and extending a second distance from the bottom wall of the housing in the first direction, the second distance being less than the first distance, the second member configured to change movement of the first member from a linear first direction of movement of the first member to a second direction of movement of the first member before the first member contacts the stop;
wherein the second direction of movement of the first member includes a component transverse to the first direction of movement of the first member.

2. The instrument of claim 1, wherein the second member comprises a raised portion configured to contact the movable first member.

3. The instrument of claim 2, wherein the raised portion is off-centered relative to a longitudinal axis of the instrument.

4. The instrument of claim 1, wherein the housing comprises a recessed portion capable of accommodating a portion of the movable first member.

5. The instrument of claim 4, wherein the recessed portion is on a side wall of the housing.

6. The instrument of claim 1, further comprising a cannula having a portion in the housing, and a movable third member connected to the cannula, wherein the second member is between the moveable first member and the moveable third member.

7. The instrument of claim 6, further comprising a pivotable latch capable of holding and releasing the movable third member.

8. The instrument of claim 1, further comprising a pivotable latch capable of holding and releasing the movable first member.

9. The instrument of claim 8, further comprising a first trigger capable of engaging the pivotable latch to release the movable first member.

10. The instrument of claim 9, further comprising a second trigger capable of engaging the pivotable latch to release the movable first member.

11. The instrument of claim 9, wherein the first trigger is located at a distal end of the housing.

12. The instrument of claim 9, wherein the first trigger is located between a distal end and a proximal end of the housing.

13. A medical instrument, comprising:
a housing;
a movable stylet block in the housing;
a stylet connected to the stylet block;
a movable cannula block in the housing;
a cannula connected to the cannula block; and
a stop between the stylet block and the cannula block, the stop having a planar first portion and a second portion extending axially away from the first portion towards the stylet block, the second portion spaced apart from the stylet block, wherein the stop is configured such that the stylet block sequentially contacts the second portion of the stop then the first portion of the stop.

14. The instrument of claim 13, wherein the first portion of the stop is in contact with and extends a first distance from a wall of the housing in a first direction and the second portion of the stop is in contact with and extends a second distance from the wall of the housing in the first direction, the second distance being less than the first distance.

15. The instrument of claim 13, wherein the housing comprises a recessed portion configured to accommodate a portion of the stylet block.

16. The instrument of claim 13, further comprising a pivotable latch capable of holding and releasing the cannula block.

17. The instrument of claim 13, further comprising a pivotable latch capable of holding and releasing the stylet block.

18. The instrument of claim 17, further comprising two triggers, either trigger capable of pivoting the latch to release the stylet block.

* * * * *